United States Patent [19]

Budde

[11] Patent Number: 5,072,048

[45] Date of Patent: Dec. 10, 1991

[54] PROCESS FOR THE RECOVERY OF ETHYLENE AMINES

[75] Inventor: Frederik J. Budde, Md Hengelo, Netherlands

[73] Assignee: Akzo N.V., Netherlands

[21] Appl. No.: 415,810

[22] Filed: Oct. 2, 1989

[30] Foreign Application Priority Data

Oct. 5, 1988 [NL] Netherlands .......................... 8802437

[51] Int. Cl.$^5$ ............................................ C02C 209/00
[52] U.S. Cl. ..................................... 564/498; 564/497
[58] Field of Search ................................. 564/498, 497

[56] References Cited

U.S. PATENT DOCUMENTS 2,362,579 11/1944 Murray et al. ...................... 260/583
3,433,788 3/1969 Somekh et al. ..................... 260/247
4,683,337 7/1987 Budde ................................. 564/498

FOREIGN PATENT DOCUMENTS 0546523 3/1979 Japan .

*Primary Examiner*—Glennon H. Hollrah
*Assistant Examiner*—Peter G. Sullivan
*Attorney, Agent, or Firm*—David H. Vickrey; Louis A. Morris

[57] ABSTRACT

A process is disclosed for the extraction recovery of ethylene amines from an aqueous solution containing at least 10% by weight sodium chloride and not more than 5% by weight sodium hydroxide, the process comprised of mixing with said aqueous solution an extraction-effective amount of a polar organic solvent which is immiscible with an aqueous salt solution, miscible with water and having a boiling poing below about 105° C. This mixture is allowed to form an organic phase and an aqueous salt solution phase. The organic phase, which contains at least a portion of the ethylene amines, is separated from the aqueous salt solution phase. The preferred polar organic solvent is n-propanol. The preferred temperature range for the process is between about 70° C. and about 95° C.

3 Claims, No Drawings

PROCESS FOR THE RECOVERY OF ETHYLENE AMINES

BACKGROUND OF THE INVENTION

The invention relates to a process for the recovery by extraction of ethylene amines from a sodium chloride-containing solution, using a polar organic solvent which is immiscible with an aqueous salt solution, water-miscible and has a boiling point below 105° C.

Such a process is known from the Japanese Patent Application published under no. 6523/'79. In this patent specification a process is described for extracting ethylene amines from an aqueous sodium chloride-containing solution using caustic soda and an organic solvent. According to the teaching of said patent specification the concentration of caustic soda in the solution must be at least 15% by weight for merely adequate extraction, but for favorable extraction a concentration in the range of 25-45% by weight is required. Mentioned as organic solvents are alcohols having 3 to 6 carbon atoms, dioxane, pyridine, and picolines. The resulting caustic soda solution is contaminated with a small amount of dissolved salt and solvent, rendering it unattractive for any other purpose. Another drawback is that the concentrated caustic soda solution is diluted significantly by its being added to the aqueous extraction mixture, so that it will be necessary to concentrate the sodium hydroxide solution by evaporation after its separation from the mixture in order to render it suitable for reuse in the extraction process. A further drawback is the precipitation of much sodium chloride from the extraction mixture as a result of the addition of caustic soda. This severely impurified precipitate consists primarily of very small salt particles which are difficult to purify and process.

From EP-A 0 110 470 it is known to extract ethylene amines using water-insoluble solvents. However, the separation by distillation of the obtained ethylene amines and solvent is very cumbersome if use is made of lower, water-immiscible alcohols as a result of a so-called maximum boiling point azeotrope being formed, and, more important, due to the boiling points of the alcohol and ethylene diamine being similar. The presently proposed invention provides a comparatively simple and economical technique for recovering ethylene amines from a salt-containing solution.

SUMMARY OF THE INVENTION

The invention is, in one embodiment, a process for the recovery by extraction of ethylene amines from an aqueous solution containing at least 10% by weight sodium chloride and not more than 5% by weight sodium hydroxide, the process comprised of mixing with said aqueous solution an extraction-effective amount of a polar organic solvent to produce a mixture, said polar organic solvent being immiscible with an aqueous salt solution, miscible with water and having a boiling point below about 105° C., allowing said mixture to form an organic phase and an aqueous salt solution phase, said organic phase containing at least a portion of said ethylene amines, and separating said organic phase and said aqueous salt solution phase. The preferred polar organic solvent is n-propanol.

DETAILED DESCRIPTION OF THE INVENTION

The invention relates to a process for the recovery by extraction of ethylene amines from an aqueous solution containing at least 10 wt. % sodium chloride and not more than 5% by weight of sodium hydroxide. The extraction is carried out using a polar organic solvent which is immiscible with an aqueous salt solution, water-miscible and has a boiling point less than about 105° C. By the term water-miscible is meant here that at room temperature at least 15% of the organic solvent will be fully mixed with water. It has been found that the extraction proceeds satisfactorily if organic solvents of the type described hereinbefore are added without the mixture to be extracted requiring any other additive. Examples of such solvents include n-propanol, isopropanol, tertiary butanol, and propanone. Particularly favorable results are obtained if the solvent used is n-propanol. The use of such organic solvents makes it possible to obtain a favorable distribution coefficient in the mixture, and the separation of the obtained alcohol-containing extraction liquid can be carried out in a relatively simple manner. The distribution coefficient is defined as:

$$\frac{\text{amount of amine (in g) in the amine-free organic liquid (in kg)}}{\text{amount of amine (in g) in the amine-free salt-containing liquid (in kg)}}$$

In the distribution coefficient definition, "amine-free" liquid means a liquid minus the amount of amine contained in the liquid.

Said solvents have a boiling point distinctively below that of the ethylene amines, so that following extraction they may be separated from the amines by distillation. Ethylene amines may be prepared in a conventional manner by reacting 1,2-dichloroethane with ammonia. In this process hydrogen chloride is formed as a by-product of the reaction and in part reacts almost immediately with the ammonia present to form ammonium chloride. This mixture is then neutralized in a conventional manner by adding alkali hydroxide, preferably caustic soda, in stoichiometric amount, whereupon the ammonia evolved in this process is removed, and the mixture to be extracted is obtained. In the present process a small excess of caustic soda, generally less than 1%, preferably less than 0.6%, may be added to improve neutralization. As a result, the thus obtained mixture to be extracted can contain a small amount of sodium hydroxide up to a maximum of 5% by weight without the drawbacks referred to hereinbefore occurring.

The mixture to be extracted contains at least 10% by weight of sodium chloride, but preferably as much of it as is possible without any salt precipitating. In case isopropanol and propanone are used, mixtures containing over 20% by weight of sodium chloride are preferred. Optimum extraction results are obtained using a nearly saturated salt solution. In addition to sodium chloride the mixture may contain other salts, such as KCl, CaCl$_2$, or NH$_4$Cl.

Such a mixture is suitably extracted by adding at least 80% by weight of an organic solvent at a temperature above about 15° C., preferably in the range of 70° to 95° C., and more particularly at a temperature in the range of 80° to 90° C. It is preferred that this solvent should also contain some water, preferably more than 8% by weight. After the solvent has been added, the mixture may be allowed to stand, two layers being formed shortly thereafter. Preference is therefore given to multi-stage extraction, more particularly to multi-stage counter-current extraction, which latter method has proved highly suited to be used in actual practice. The two liquid phases separated in one of these ways may subsequently be further processed in a conventional manner. Thus the solvent may be removed from one phase containing salt, water, and some solvent remainder by steam stripping. The remaining salt solution, which contains practically no amines anymore after multi-stage extraction, can be further processed without any problems into a serviceable salt product. Also, the salt solution may be processed as a waste product in a conventional manner without causing environmental problems.

The other phase, which contains amines, solvent, and water, can be separated into various constituents by distillation. Such a distillation process can be carried out under normal pressure. Since most ethylene amines have a boiling point which is significantly higher than that of the solvent used, concentrations of amines of up to 100 wt. % can be obtained. If the mixture to be distilled is a mixture containing n-propanol and ethylene diamine, a concentration of over 50 wt. % can be obtained at normal pressure. If a virtually pure amine mixture is desired, it is recommended to raise the pressure during distilling to above 5 atm., preferably to above 8 atm. The "amine mixture" contains, at a minimum, ethylene diamine, and may contain other amines, such as diethylene triamine, triethylene tetraamine and tetraethylene pentamine. The thus resulting amine mixture can be separated into constituents by distillation.

The solvent which was also separated by distillation may be reused in the extraction process.

EXAMPLES

Example 1

(a) 100 cc of an aqueous solution containing 8.7 g of ethylene diamine per kg of solution and 23 wt. % of NaCl was mixed at 80° C. with 75 cc of a mixture of n-propanol and 10 wt. % of water. Almost immediately two layers were formed, which were next separated and analyzed. The organic layer contained 5.0 g of ethylene diamine per kg of liquid. The aqueous salt solution contained 6.4 g of ethylene diamine per kg of liquid. The distribution coefficient therefore was 0.78. A mixture of ethylene diamine and n-propanol was distilled at a pressure of 8 atm after which the ethylene diamine obtained contained less than 10 ppm of n-propanol.

(b) The same test as described in 1(a) was carried out at 25° C. The distribution coefficient this time was 0.48.

Example 2

The same test as described in Example 1(a) was repeated, except that this time 100 cc of solutions containing 23 wt. % of NaCl and 0.2, 1, 10, and 15% by weight, respectively, of ethylene diamine were mixed with 75 cc of the solution containing n-propanol and 10 wt. % of water. After separation of the layers a distribution coefficient of 0.765±0.015 was found in each case.

Example 3

The same test as described in Example 1(a) was carried out five times, using a different amine each time. In this process in all cases 100 cc of a 23 wt. %-NaCl solution containing 1 wt. % of ethylene amine were extracted with 75 cc of the same n-propanol solution.

After separation of the layers the following distribution coefficients were obtained by extraction:
(a) diethylene tetramine 0.87
(b) triethylene tetramine 1.30
(c) tetraethylene pentamine 1.47
(d) diethylene diamine 1.92
(e) 2-normal-amine-ethyle-piperazine 2.12

Example 4

(a) 100 cc of a solution containing 5 wt. % of ethylene diamine and 23 wt. % of NaCl were mixed at 80° C. with 75 cc of a mixture of isopropanol and 10 wt. % of water. Two layers formed almost immediately. They were separated and analyzed. The distribution coefficient was 0.57. Virtually 100% pure ethylene diamine can be obtained by distillation at a pressure of 1 atm.

(b) The same test as described in 4(a) was carried out at 25° C. The distribution coefficient found was 0.48.

Example 5

The test as referred to in Example 4(b) was carried out this time with a mixture of 2-propanone and 10% by weight of water at 25° C. After separation of the almost immediately formed layers, a distribution coefficient of 0.41 was measured.

The results show that extraction using water-miscible solvents without any other additive proceeds favorably in all cases. Distillation of the organic layer can be carried out without expensive distillation equipment being required. In case n-propanol is the extraction solvent, very good extraction results are obtained. In that case the final distillation step for recovering ethylene diamine is carried out at a pressure of 8 atm. In all cases it is preferred that the salt-containing layer should be extracted by a multi-stage extraction process.

Example 6

Charged countercurrently into a 4-stage extraction apparatus of the mixer-settler type at a temperature of 70° C. and atmospheric pressure were 31 kg/hr of an aqueous solution of 14 wt. % of ethylene diamine and 23 wt. % of NaCl, and 93 kg/hr of a mixture of n-propanol and 12.5 wt. % of H$_2$O. The discharged salt-containing phase contained 0.2% wt. % of ethylene diamine and the organic phase 4.5 wt. %. Thus, 98.6% of the ethylene diamine in the initial salt solution had passed into the organic phase.

COMPARATIVE EXAMPLE 1

A solution containing ethylene amines and salt was obtained in the conventional manner by reacting dichloroethane with ammonia, followed by neutralization with a 48 wt. % NaOH solution. The resulting solution contained 13.4 wt. % of ethylene amines and 28.6 wt. % of NaCl. It was mixed with a 48 wt. % NaOH solution and a mixture of isopropanol and 23 wt. % of ethylene amines. This mixture formed 2 layers, which were separated. The organic layer contained 53.7 wt. % of ethylene amines and 28.2 wt. % of isopropanol. In the salt-containing aqueous slurry was also present as by-product a solid, finely dispersed NaCl. This NaCl contains isopropanol, NaOH, and a comparatively large amount of amines (1.5%). Separation and washing proved difficult on account of the small particle size and the amines being incorporated into the salt crystals. After extraction the high-grade caustic soda solution was found to have been diluted to about 30%. In addition, the caustic soda contained isopropanol and NaCl. It was found to be impossible to recover a similar quality of caustic soda even after purification owing to the remaining impurification caused by the remaining NaCl, while increasing the concentration by evaporation is very energy consuming.

COMPARATIVE EXAMPLE 2

100 cc of a solution containing 5 wt. % of ethylene diamine and 23 wt. % of NaCl were mixed at 80° C. with 75 cc of a mixture of isobutanol and 10 wt. % of water. After two layers had formed almost immediately, they were separated and analyzed. The distribution coefficient found was 0.57. Purification by distillation of the obtained alcohol-containing extraction mixture (the organic layer) is found to be very difficult due to the reasons given before without use of special and expensive distillation equipment.

COMPARATIVE EXAMPLE 3

The same test as described in Example 2 was carried out at 80° C., except that n-butanol was employed. The coefficient of dispersion found in this case was 0.56, and further separation by distillation of the ethylene diamine from the organic layer is found almost impossible.

These examples show that extraction using the higher alcohols (alcohols having a boiling point greater than about 105° C.) produces a less favorable result, since separating the desired ethylene amine from the extraction agent is an extremely cumbersome process, if it can be done at all.

I claim:

1. A process for the recovery by extraction by ethylene amines from an aqueous solution containing at least 10% by weight sodium chloride and not more than 5% by weight sodium hydroxide, the process comprising of mixing with said aqueous solution an extraction-effective amount of a polar organic solvent to produce a mixture, said polar organic solvent being selected from the group consisting of n-propanol, isopropanol, tertiary butanol, 2-propanone and mixtures thereof, allowing said mixture to form an organic phase and an aqueous salt solution phase, said organic phase containing at least a portion of said ethylene amines and separating said organic phase and said aqueous salt solution phase.

2. The process of claim 1 wherein the polar organic solvent is n-propanol.

3. The process of claim 1 wherein the temperature during the process is in the range of about 70° C. to about 95° C.

* * * * *